United States Patent [19]
Causey, III et al.

[11] Patent Number: 5,792,201
[45] Date of Patent: Aug. 11, 1998

[54] SAFETY OPTIMIZATION IN MICROPROCESSOR-CONTROLLED IMPLANTABLE DEVICES

[75] Inventors: James D. Causey, III, Simi Valley; Min-Yaug Yang, Monterey Park, both of Calif.

[73] Assignee: Pacesetter, Inc., Sylmar, Calif.

[21] Appl. No.: 749,579

[22] Filed: Nov. 15, 1996

Related U.S. Application Data

[62] Division of Ser. No. 501,838, Jul. 13, 1995, Pat. No. 5,607,458.

[51] Int. Cl.⁶ .................................................. A61N 1/37
[52] U.S. Cl. .................................................... 607/27
[58] Field of Search ............................ 607/4, 5, 9, 11, 607/15, 27–29, 63

[56] References Cited

U.S. PATENT DOCUMENTS

| | | |
|---|---|---|
| 4,256,115 | 3/1981 | Bilitch ........................ 607/9 |
| 4,390,022 | 6/1983 | Calfee et al. . |
| 4,485,818 | 12/1984 | Leckrone et al. . |
| 4,539,991 | 9/1985 | Boute et al. . |
| 4,726,380 | 2/1988 | Vollmann et al. . |
| 4,875,483 | 10/1989 | Vollmann et al. . |
| 4,944,298 | 7/1990 | Sholder . |
| 4,958,632 | 9/1990 | Duggan . |
| 5,273,035 | 12/1993 | Markowitz et al. ........ 607/14 |
| 5,464,435 | 11/1995 | Neumann ..................... 607/9 |
| 5,496,349 | 3/1996 | Campbell et al. ........... 607/5 |
| 5,571,141 | 11/1996 | McNeil et al. ............... 607/5 |

*Primary Examiner*—Jeffrey R. Jastrzab

[57] ABSTRACT

A microprocessor-controlled implantable cardiac stimulating device having a normal mode, an intermediate mode, and a backup pacing mode is provided. The device switches from one mode to another in response to the detection of any one of an address error, parity error, opcode error, or watchdog timer error. The microprocessor is shut down during the delivery of a cardioversion or defibrillation shock in order to prevent signals produced by the microprocessor from being subjected to transient electrical signals. The interrupt registers of the microprocessor are also disabled during the delivery of a cardioversion or defibrillation shock. In an alternative embodiment, an implantable cardiac stimulating device is provided with redundant microprocessors in order to detect malfunctions of the microprocessors.

6 Claims, 10 Drawing Sheets

SAFETY OPTIMIZATION IN MICROPROCESSOR-CONTROLLED IMPLANTABLE DEVICES

This is a divisional of application Ser. No. 08/501,838 filed on Jul. 13, 1995, now U.S. Pat. No. 5,607,458.

FIELD OF THE INVENTION

This invention relates to microprocessor-controlled implantable medical devices, and particularly to microprocessor-controlled implantable cardiac stimulating devices. More particularly, this invention relates to safety optimization apparatus and methods for use in microprocessor-controlled implantable cardiac stimulating devices.

BACKGROUND OF THE INVENTION

Implantable cardiac stimulating devices which provide electrical stimulation in response to a variety of pathological cardiac arrhythmias are known. Some implantable cardiac stimulating devices provide "tiered therapy," in which the type of electrical stimulation provided is determined in accordance with the severity of the arrhythmia, with more aggressive therapies being applied in response to more severe arrhythmias. For example, such devices may respond to relatively less severe forms of tachycardia by delivering antitachycardia pacing pulses of about 25 µjoules to about 30 µjoules in a sequence known to interrupt such episodes. In response to relatively more severe forms of tachycardia, the implantable cardiac stimulating device may deliver a low energy cardioversion shock on the order of about 2 joules to about 5 joules, either in combination with, or as an alternative to, antitachycardia pacing pulses. In response to an occurrence of an even more severe arrhythmia, for example, ventricular fibrillation, the implantable cardiac stimulating device may deliver a high energy defibrillation shock on the order of about 10 joules to about 40 joules.

Implantable cardiac stimulating devices which provide pacing pulses to cardiac tissue to maintain a heart rate at a physiologically acceptable rate (i.e., to provide "bradycardia pacing support") are also known. Bradycardia pacing support may be provided by a dedicated pacemaker, or by a device that is also capable of providing other forms of therapy, such as tiered therapy.

Implantable cardiac stimulating devices typically contain a microprocessor to control the administration of the various pacing therapies and cardioversion and defibrillation shocks. Implantable cardiac stimulating devices typically may store preprogrammed information, and physiological and electrophysiological information gathered from the patient's heart, in one or more memory devices contained within the device.

If data stored in a memory device are unexpectedly altered or corrupted, inappropriate pacing may be administered to the patient's heart with possible adverse effects. For example, corrupted data may cause the device to fail to provide pacing pulses, or may cause the device to deliver a defibrillation shock at an inappropriate time. Malfunction of the microprocessor may also cause an inappropriate form of therapy to be delivered.

Microprocessor malfunction and corruption of data stored in memory devices can occur for several reasons. For example, in an implantable cardiac stimulating device, power is supplied by a battery contained within the device. If the battery is unable to supply sufficient power, the memory devices or the microprocessor may not receive enough power to function correctly. This may cause data stored in memory devices to be lost or altered, or may cause the microprocessor to malfunction.

Memory devices in an implantable device also may not function properly if they are subjected to x-rays, microwave radiation, or magnetic fields while implanted within the patient. For example, a patient may receive x-rays which may cause data stored in memory devices to be altered. As another example, the patient may pass through a strong magnetic field which may cause data to be altered. Random access memory devices (RAM) may be particularly sensitive to these sources of errors.

Calfee et al. U.S. Pat. No. 4,390,022 ("the '022 patent") describes an implantable cardiac pacer that verifies the parity of a 7-bit instruction byte stored in RAM in order to detect a possible error in the instruction byte. The '022 patent describes an eighth bit in addition to the 7-bit instruction byte to indicate the parity of the instruction byte. However, the described method suffers from certain disadvantages. For example, the described method only checks the parity of the 7-bit instructions stored in RAM. The '022 patent does not describe checking the parity of other data stored in RAM. In view of this drawback, it would be advantageous to provide parity checking of all data stored in RAM so as to provide greater error protection and increase the safety of the patient.

The '022 patent also describes moving the program counter of the implantable device to a fixed rate pacing program when a parity error of an instruction byte is detected. Although this may prevent the parity error from causing inappropriate pacing to be administered, it suffers from disadvantages. For example, once a single parity error in an instruction byte is detected, the device can only utilize the fixed rate program, thus limiting the patient to fixed-rate pacing. Therefore, after only a single parity error in an instruction byte is detected, the device is unable to gather information from the patient's heart or use information preprogrammed into the device. However, a single parity error does not always indicate that the memory device is defective and no longer useful. In view of these disadvantages, it would be desirable to provide a mode of operation for the implantable device which would eliminate the source of error while still allowing the microprocessor to use the memory devices.

Furthermore, the '022 patent suffers from the disadvantage that fixed rate pacing is administered by a program. The program instructions for the fixed rate pacing may themselves become corrupted, or the microprocessor which executes the program may malfunction, thereby causing even the fixed rate pacing program to fail. In view of these drawbacks, it would be advantageous to provide a pacing mode which can operate independent of the microprocessor and associated memory devices. Such a pacing mode would increase the safety of the device and reduce the likelihood of inappropriate therapy being applied to the patient's heart.

Another source of errors in implantable cardiac stimulating devices are transient electrical signals which may be generated during the delivery of cardioversion and defibrillation shocks. These transient electrical signals may cause data to be altered. It would therefore be advantageous to provide error prevention methods and apparatus which would prevent these errors.

SUMMARY OF THE INVENTION

In accordance with the present invention, an implantable cardiac stimulating device is provided having error checking apparatus and methods for determining if the device is functioning correctly. In response to the detection of an error, the device is able to switch between a normal mode, an intermediate mode, and a backup pacing mode. The intermediate mode is designed to significantly reduce the possibility of inappropriate pacing therapy being administered to the patient's heart, while still providing an advanced level of therapy.

A preferred embodiment of an implantable cardiac stimulating device constructed in accordance with the present invention has a microprocessor, a memory device coupled to the microprocessor, a pulse delivery circuit coupled to the microprocessor for delivering an electrical stimulation pulse to a patient's heart, a backup pacing circuit for delivering backup pacing to the patient's heart, and at least one error detection circuit for detecting errors in the implantable cardiac stimulating device. The device preferably has switching circuitry coupled to each of the microprocessor, the error detection circuit, and the backup pacing circuit, for switching the implantable cardiac stimulating device from a normal mode to an intermediate mode in response to a first error detected by the error detection circuit. The switching circuitry switches the implantable cardiac stimulating device from the intermediate mode to a backup pacing mode in response to a second error detected by the error detection circuit. In the normal mode, the pulse delivery circuit is controlled by the microprocessor, and the microprocessor is able to store data in and retrieve data from the memory device. In the intermediate mode, the pulse delivery circuit is still controlled by the microprocessor, and the microprocessor continues to be able to store data in the memory device. However, the microprocessor is only able to retrieve data that was stored in the memory device after the implantable cardiac stimulating device entered the intermediate mode. Thus, data which were stored in the memory device prior to entering the intermediate mode are not used by the microprocessor. In the backup pacing mode, the microprocessor is disabled and the backup pacing circuitry is activated. The backup pacing circuit preferably is a "hardwired" circuit which can operate without microprocessor intervention.

In a preferred embodiment, the implantable cardiac stimulating device is capable of detecting several different types of errors which may occur.

One type of error detection which is provided by the present invention is parity error detection. In accordance with the present invention, all data units which are stored in a RAM preferably are given parity bits. Data are preferably stored in 9-bit units in which the ninth bit indicates the parity of the other 8 bits. The present invention thus overcomes the disadvantages in previous devices because all types of data incorporate parity detection, thereby increasing the patient's safety.

Parity error detection is preferably accomplished by a parity checker. The parity checker compares the parity bit of a data unit stored in the memory device to the parity of the data bits and generates an error signal if the parity bit is not correct. If a parity error is detected while the device is in the normal mode, the device is set to the intermediate mode. If a parity error is detected while the device is in the intermediate mode, the device is set to the backup pacing mode.

Another type of error checking is provided by an address decoder. When the microprocessor attempts to access a memory location, the address decoder decodes the address and determines if the address is a proper address. If the address is not a proper address, an error signal is generated. An example of an improper address is an address which is higher than the highest valid addressable location. If the addressable location is determined to be invalid and the device is in the normal mode, the device is set to the intermediate mode. If the device is in the intermediate mode and an address error is detected, the device is set to the backup pacing mode.

Yet another type of error detection is provided by an opcode checker. Opcodes identify the instructions executed by the microprocessor. In accordance with the present invention, the opcode checker preferably operates by first receiving a signal which indicates that the microprocessor is about to fetch an opcode from the memory device. The opcode checker then determines if the opcode is a valid opcode. If the opcode is not a valid opcode an error signal is issued. An example of an invalid opcode is an opcode which is not used by the microprocessor. If the opcode is determined to be invalid and the device is in the normal mode, the device is set to the intermediate mode. If an opcode error is detected while the device is in the intermediate mode, the device is set to the backup pacing mode.

Another type of error detection is performed by a watchdog timer circuit. The watchdog timer circuit is provided in order to determine if the microprocessor is functioning correctly. In a preferred embodiment, the watchdog timer circuit also functions as the switching circuit which switches the device between the normal, intermediate, and backup modes. A preferred method of operating the watchdog timer in order to detect malfunctions of the microprocessor is as follows. First, an interrupt generating circuit provides an interrupt signal to the microprocessor. If the microprocessor is functioning correctly, it is able to communicate an acknowledgment signal to the watchdog timer circuit in response to receiving the interrupt signal. If a proper acknowledgment signal is not received by the watchdog timer circuit from the microprocessor within a predetermined interval of time after the microprocessor receives the interrupt signal, the device is switched to the backup pacing mode. Thus, detection of an error by the watchdog timer circuit causes the device to enter the backup pacing mode regardless of whether the device was operating in the normal mode or the intermediate mode when the error was detected.

In accordance with a still further safety optimization feature of this invention, the microprocessor is shut down when a cardioversion or defibrillation shock is delivered to the patient's heart. Signals generated by the microprocessor therefore are not subjected to potentially corrupting transient electrical signals. In order to accomplish this, just prior to the delivery of electrical stimulation to the patient's heart, the microprocessor programs a timer to send a wakeup signal to a system clock generator. The timer is programmed so that it sends a wakeup signal to the system clock generator a predetermined interval of time after the timer is programmed. The microprocessor then sends a signal to the system clock generator which prevents the microprocessor from receiving clock signals, thereby halting processing by the microprocessor. The cardioversion or defibrillation shock is delivered while the microprocessor is shut down. After the predetermined interval of time has elapsed (which is longer than the time it takes to deliver the cardioversion or defibrillation shock), the timer issues the wakeup signal. The wakeup signal enables the microprocessor to receive the clock signals from the system clock generator, thereby allowing processing by the microprocessor.

In addition to shutting down the microprocessor during the delivery of a cardioversion or defibrillation shock, interrupt registers of the microprocessor are disabled during delivery of a cardioversion or defibrillation shock. Prior to shutting off the clock signal, the microprocessor switches a gating circuit which disconnects the inputs of the microprocessor interrupts. The interrupt registers therefore are not subject to transient electrical signals, which may inadvertently trigger the interrupt registers.

In another embodiment, a high voltage interface circuit is used to monitor the charging of the high voltage energy in the output capacitor and/or to monitor the amount of shock delivered to the patient. If a malfunction occurs, the microprocessor is notified and appropriate action can be taken.

In an alternative embodiment, safety optimization is accomplished by providing redundant microprocessors. In this embodiment the implantable cardiac stimulating device has a first microprocessor, a second microprocessor, a comparator connected to the first and second microprocessors, an interface connected to the comparator and the first and second microprocessors, and a data bus connected to the interface. The interface receives signals from the data bus and transfers a copy of the signals to each of the first and second microprocessors. The first microprocessor processes the signals to produce a first processed signal, while the second microprocessor processes the signals to produce a second processed signal. Each of the first and second processed signals are communicated to the comparator.

The comparator compares the first and second processed signals in order to determine if the first and second microprocessors are functioning correctly.

If the signals are not substantially identical, the microprocessors are shut down and the backup pacing circuitry is activated. In this manner, an improperly functioning microprocessor may be prevented from causing improper pacing and cardioversion or defibrillation shocks to be delivered to the patient.

BRIEF DESCRIPTION OF THE DRAWINGS

The above and other objects and advantages of the present invention will be apparent upon consideration of the following detailed description, taken in conjunction with the accompanying drawings, in which like referenced characters refer to like parts throughout, and in which.

DETAILED DESCRIPTION OF THE PREFERRED EMBODIMENTS

Figure 1:
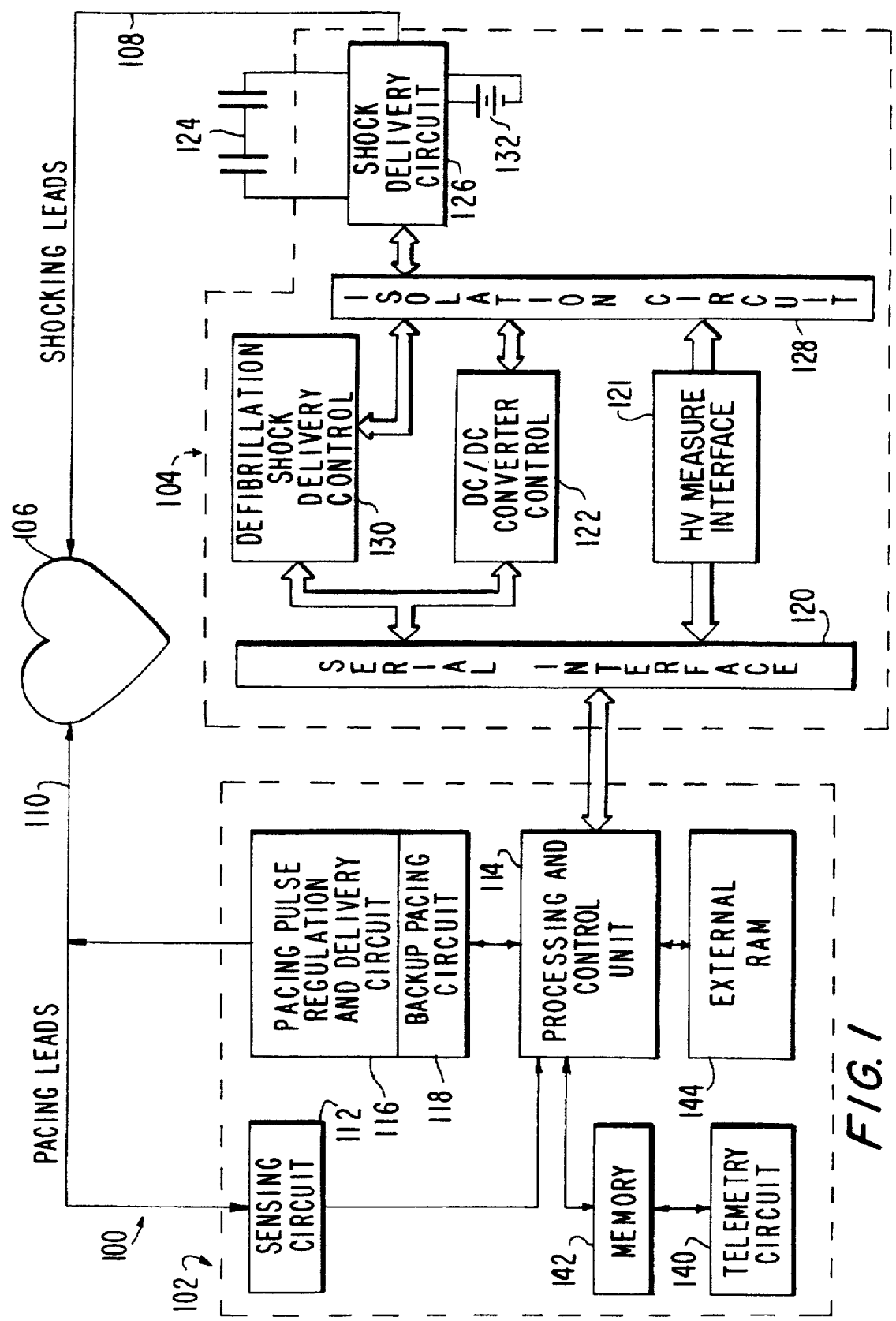
FIG. 1 is a schematic diagram of a preferred embodiment of an implantable cardiac stimulating device which includes backup pacing circuitry in accordance with the present invention.

FIG. 1 is a schematic diagram of an implantable cardiac stimulating device 100 having backup pacing circuitry in accordance with the present invention. The implantable cardiac stimulating device 100 preferably has three modes of operation—a normal mode, an intermediate mode, and a backup pacing mode. At any given time, the particular mode in which the device is operating is determined by the number and nature of errors which have been detected within the device. Before describing the modes of operation and error detection methods and circuitry, a general description of device 100 is provided so that the features and advantages of the invention may be better understood.

The implantable cardiac stimulating device 100 includes circuitry 102 which is responsible for regulation and delivery of pacing therapy as well as overall operational control of the device 100. Also included is circuitry 104 dedicated to the control, generation, and delivery of cardioversion and defibrillation shocks. The implantable cardiac stimulating device 100 preferably administers therapeutic shocks (i.e., cardioversion or defibrillation shocks) or pacing pulses to a patient's heart 106 in order to interrupt cardiac arrhythmias or supply artificial pacing, respectively. However, the present invention also may be practiced with dedicated implantable cardioverters and defibrillators, as well as dedicated implantable pacing devices.

The implantable cardiac stimulating device 100 administers therapeutic shocks to the patient's heart 106 through a plurality of shocking leads 108. Pacing pulses are delivered to the patient's heart 106 through a pacing lead system 110. However, the therapeutic shocks and pacing pulses may be delivered through the same leads (not shown). The pacing lead system 110 also serves to sense intrinsic cardiac activity during periods when electrical stimulation is not being applied to the heart. The lead system 110 feeds physiological and electrophysiological data in the form of analog signals from the patient's heart 106 to a sensing circuit 112. Furthermore, the implantable cardiac stimulating device 100 is preferably enclosed within an electrically conductive case (not shown) which may be used as an electrode in the delivery of pacing pulses.

The sensing circuit 112 typically amplifies the incoming analog signals and filters out unwanted noise. The amplified signals are then digitized and formatted for use by a processing and control unit 114. The processing and control unit 114 analyzes the digital signals in order to determine the appropriate therapy.

The processing and control unit 114 communicates with a pacing pulse regulation and delivery circuit 116 which generates and transmits electrical pulses to the patient's heart 106. The pacing pulse regulation and delivery circuit 116 includes a backup pacing circuit 118 for use as described in detail below. The processing and control unit 114 determines the appropriate lead or leads of the lead system 110 through which the therapy is delivered.

In order to deliver a cardioversion or defibrillation shock, the processing and control unit 114, through a serial interface 120, instructs a DC/DC converter control circuit 122 to begin charging a pair of capacitors 124 in series with each other to a target voltage. The DC/DC converter control circuit 122 in turn, instructs a shock delivery circuit 126, through an isolation circuit 128, to begin charging the capacitors 124. The DC/DC converter control circuit 122 performs the control and logic operations needed by the shock delivery circuit 126 to create a high frequency oscillated high voltage for application to the capacitors 124. A defibrillation shock delivery control circuit 130 performs the logic and control operations needed to deliver a desired therapeutic shock to the patient's heart 106.

In a preferred embodiment, the isolation circuit 128 includes a transformer interface (not shown) which is used to electrically isolate the low voltage circuits of both the defibrillation shock delivery control circuit 130 and the DC/DC converter control circuit 122 as well as the circuitry 102 from exposure to high voltages.

Once the defibrillation shock delivery control circuit 130 is informed that capacitors 124 are sufficiently charged, the processing and control unit 114 then instructs the defibrillation shock delivery control circuit 130 to direct the shock delivery circuit 126 to administer the shock to the patient's heart 106.

A high voltage interface circuit 121 is used to monitor the charging of high voltage energy in the output capacitors 124 and/or are capable of monitoring the amount of shock delivered to the patient. If any malfunction occurs, the microprocessor is notified. Depending on the type of failure, the microprocessor can convey the problem at the next interrogation, activate an annunciator to alert the patient to see his physician, and potentially shut down the defibrillation shock delivery control circuit 130.

Communication with and programming of the implantable cardiac stimulating device 100 is accomplished by a programmer (not shown) which communicates with the device 100 through a telemetry circuit 140. Telemetry data is transmitted to the processing and control unit 114 through a memory 142.

An external RAM 144 connected to the processing and control unit 114 is provided for storing data.

Figure 2:
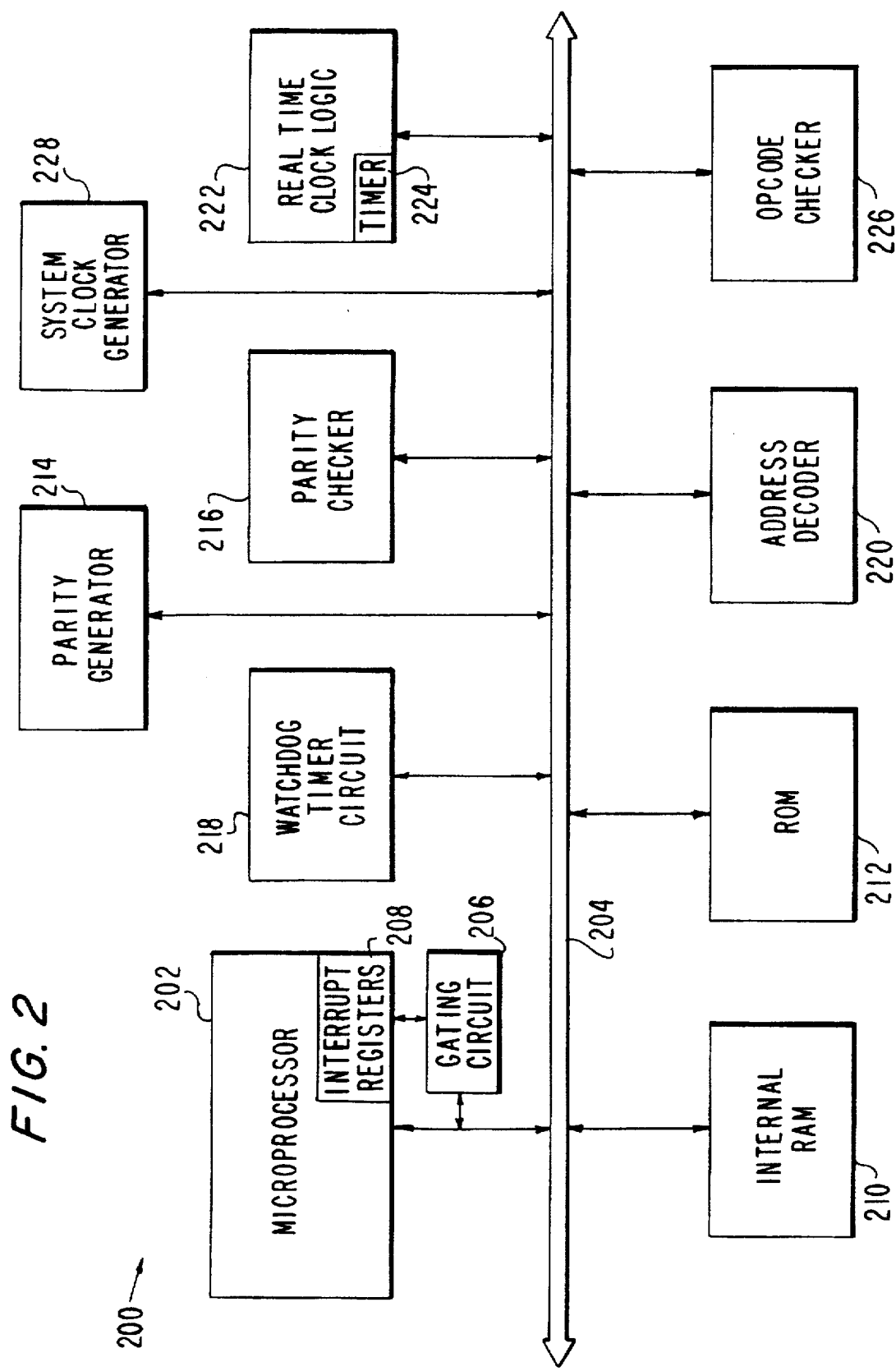
FIG. 2 is a schematic diagram showing the processing and control unit of FIG. 2 including fault detection circuitry in accordance with the present invention.

FIG. 2 shows a processing and control unit 200 (suitable for use as the processing and control unit 114 of FIG. 1) constructed in accordance with the present invention. The processing and control unit 200 includes a microprocessor 202 which is connected to a data bus 204. A gating circuit 206 which is controlled by the microprocessor 202 controls access to interrupt registers 208 of the microprocessor 202. An internal RAM 210 and a ROM 212 are provided for storing data. A parity generator 214, a parity checker 216, a watchdog timer circuit 218, an address decoder 220, a real time clock logic 222, a timer 224, an opcode checker 226, and a system clock generator 228 are provided for error checking. The data bus 204 communicates with the sensing circuit 112, the pacing regulation and delivery circuit 116, the memory 142, the external RAM 144, and the serial interface 120 shown in FIG. 1.

In addition to reading data from the ROM 212, the processing and control unit 200 can read data from and write data to the external RAM 144 (FIG. 1), and the internal RAM 210. Typically, the external RAM 144 (FIG. 1) has a larger storage capacity than the internal RAM 210. Although FIG. 1 shows an implantable cardiac stimulating device 100 having the external RAM 144, in an alternative embodiment (not shown) the external RAM 144 could be eliminated in order to increase processor speed, reduce power consumption and reduce the overall size of the implantable device.

The interaction of the processing and control unit 200 with the various memory storage devices is dependent on the mode in which the implantable cardiac stimulating device is operating. In a preferred embodiment of the present invention, there are three modes of operation available to the implantable cardiac stimulating device 100—the normal mode, the intermediate mode, and the backup pacing mode.

In the normal mode the microprocessor 202 is able to use data and instructions stored in the ROM 212, the internal RAM 210, and the external RAM 144 (FIG. 1). The microprocessor 202 is able to store data in the internal RAM 210 and the external RAM 144 (FIG. 1), and is able to read data from the internal RAM 210, the external RAM 144 (FIG. 1), and the ROM 212. Program instructions and data which are provided by the programmer (not shown) via the telemetry 140 (FIG. 1) can be stored in and then retrieved from the internal RAM 210 and the external RAM 144 (FIG. 1). The microprocessor 202 also can store and then retrieve physiological and electro-physiological data gathered by the sensing circuit 112 (FIG. 1) in the internal RAM 210 and the external RAM 144 (FIG. 1). In the normal mode the implantable cardiac stimulating device 100 is therefore able to provide the most advanced level of pacing therapy. In particular, the pacing therapy may be programmed by a physician to be especially suited to the needs of the patient under treatment, and may also be adjusted in accordance with data gathered from the patient's heart by the device.

If an address, parity, or opcode error (each of which is described below) is detected while the implantable cardiac stimulating device 100 is in the normal mode, the device 100 is set to the intermediate mode either by the watchdog timer circuit 218 or other switching circuitry (not shown). Upon entering the intermediate mode, all information stored in the internal RAM 210 and the external RAM 144 (FIG. 1) is considered corrupt. Thus, although the microprocessor 202 can still use the internal RAM 210 and the external RAM 144 (FIG. 1) to store and retrieve information while in the intermediate mode, any information already stored at the time the device is switched to the intermediate mode is ignored by the microprocessor 202 and may be over-written. In the intermediate mode, the microprocessor can, for example, use the internal RAM 210 or the external RAM 144 (FIG. 1) as a scratch pad to perform a calculation, or to store data gathered from the patient's heart 106. However, the microprocessor 202 will ignore data which was stored in the internal RAM 210 or the external RAM 144 (FIG. 1) prior to entering the intermediate mode. In the intermediate mode, the microprocessor 202 is able to retrieve data from the ROM 212.

The intermediate mode thus overcomes the disadvantages of previous devices of switching directly to a fixed rate program upon detecting a single parity error. In the device 100 of the present invention, the detection of a parity error causes the microprocessor 202 to consider data stored in the internal RAM 210 and the external RAM 144 (FIG. 1) corrupt. The microprocessor 202 can, however, continue to use the internal RAM 210 and the external RAM 144 (FIG. 1).

If any of an address, parity, or opcode error is detected while in the intermediate mode, the device 100 is set to the backup pacing mode. Furthermore, if a watchdog time-out occurs or a system interrupt is telemetrically issued while the device 100 is in the intermediate mode or the normal mode, the device 100 is set to the backup pacing mode.

In the backup pacing mode the microprocessor 202 is disabled and the backup pacing circuit 118 (FIG. 1) of pacing pulse regulation and delivery circuit 116 (FIG. 1) is activated. The backup pacing circuit 118 (FIG. 1) administers backup pacing to the patient's heart until an appropriately qualified person can service the device.

The backup pacing circuit 118 (FIG. 1) preferably is a dedicated circuit that does not require the input of any signals from the microprocessor 202 in order to function. In a preferred embodiment, the backup pacing circuit 118 (FIG. 1) provides VVI pacing therapy. In VVI pacing, if a heartbeat signal is not detected from the patient's ventricle during a fixed interval of time following the previous heartbeat, whether intrinsic or paced, a pacing pulse is delivered to the ventricle of the patient's heart 106.

By providing a dedicated backup pacing circuit 118 (FIG. 1) that does not require intervention by the microprocessor 202, the disadvantages of previously known devices are overcome. In particular, the backup pacing circuit 118 (FIG. 1) is highly reliable and cannot be disrupted by malfunction of the microprocessor 202 or corruption of data stored in the internal RAM 210 and the external RAM 144 (FIG. 1).

The error detection methods and circuitry used to determine the mode of operation of the implantable cardiac stimulating device 100 are now described.

In order to detect possible errors of the microprocessor 202 and related circuitry and to increase the safety of device 100, the watchdog timer circuit 218 and the real time clock logic 222 are provided. In addition to providing error detection, the watchdog timer circuit 218 preferably also controls the switching of the device 100 between modes as described below.

Figure 3:
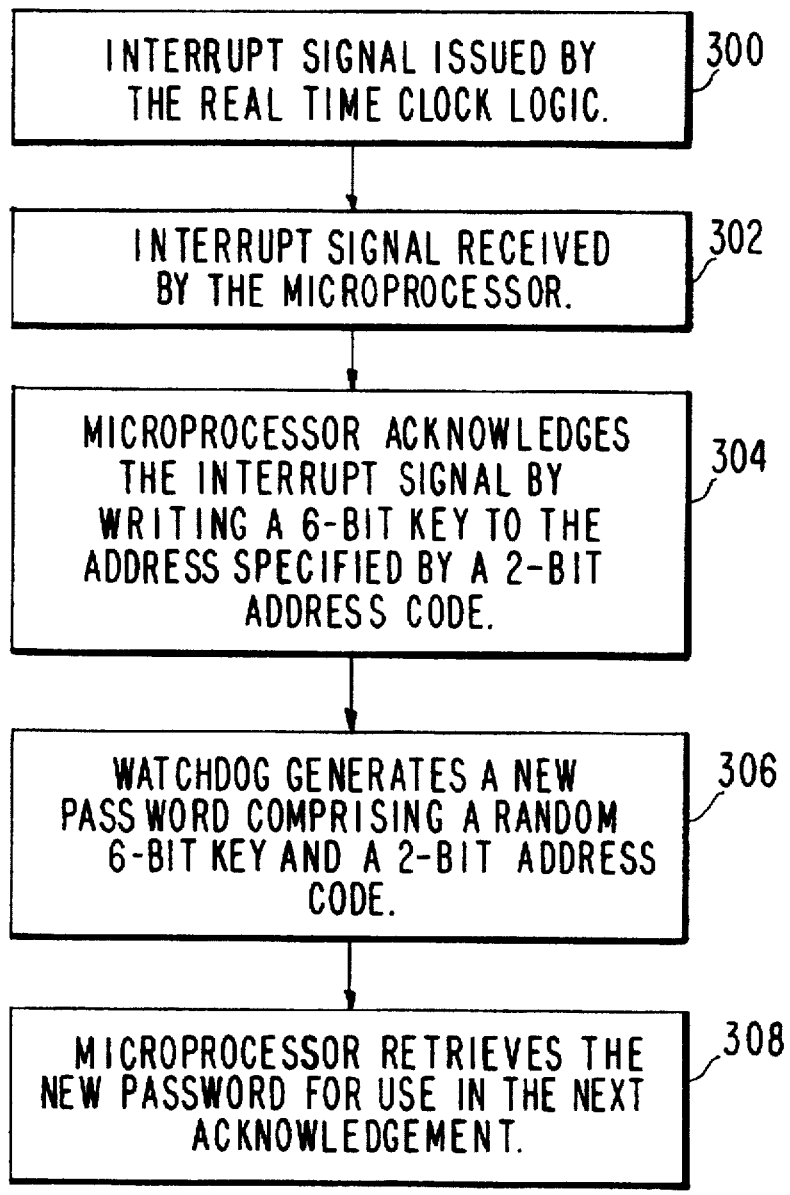
FIG. 3 is a flow diagram of steps performed by the microprocessor shown in FIG. 2 in order to respond to the watchdog timer circuit shown in FIG. 2.

FIG. 3 shows the steps carried out by the microprocessor 202 (FIG. 2) in responding to the watchdog timer circuit 218 (FIG. 2). The microprocessor 202 (FIG. 2) preferably is expected to respond to an interrupt signal which is preferably issued every two seconds by the real time clock logic 222 (FIG. 2) at step 300. The interrupt signal is received by the watchdog timer circuit 218 (FIG. 2) and the microprocessor 202 (FIG. 2). Upon receiving the interrupt signal at step 302, the microprocessor 202 (FIG. 2) sends an acknowledgment signal at step 304 to the watchdog timer circuit 218 (FIG. 2) before the next interrupt signal is issued by the real time clock logic 222 (FIG. 2). The acknowledgment signal preferably comprises an 8-bit password comprising a randomly generated 6-bit key and a 2-bit address code. The 2-bit address code specifies one of four possible addresses within the watchdog timer circuit 218 (FIG. 2), while the 6-bit key is a randomly generated code. In order to properly acknowledge the interrupt, the microprocessor 202 (FIG. 2) provides the 6-bit key to the address specified by the 2-bit address code. Each time the microprocessor 202 (FIG. 2) provides acknowledgment to the watchdog timer circuit 218 (FIG. 2), the watchdog timer circuit 218 (FIG. 2) generates a new password comprising a new key and a new address code at step 306. The microprocessor 202 (FIG. 2) retrieves this password for use in the next acknowledgment at step 308. The initial password after a system reset is an 8-bit password in which all bits are "zeros."

Figure 4:
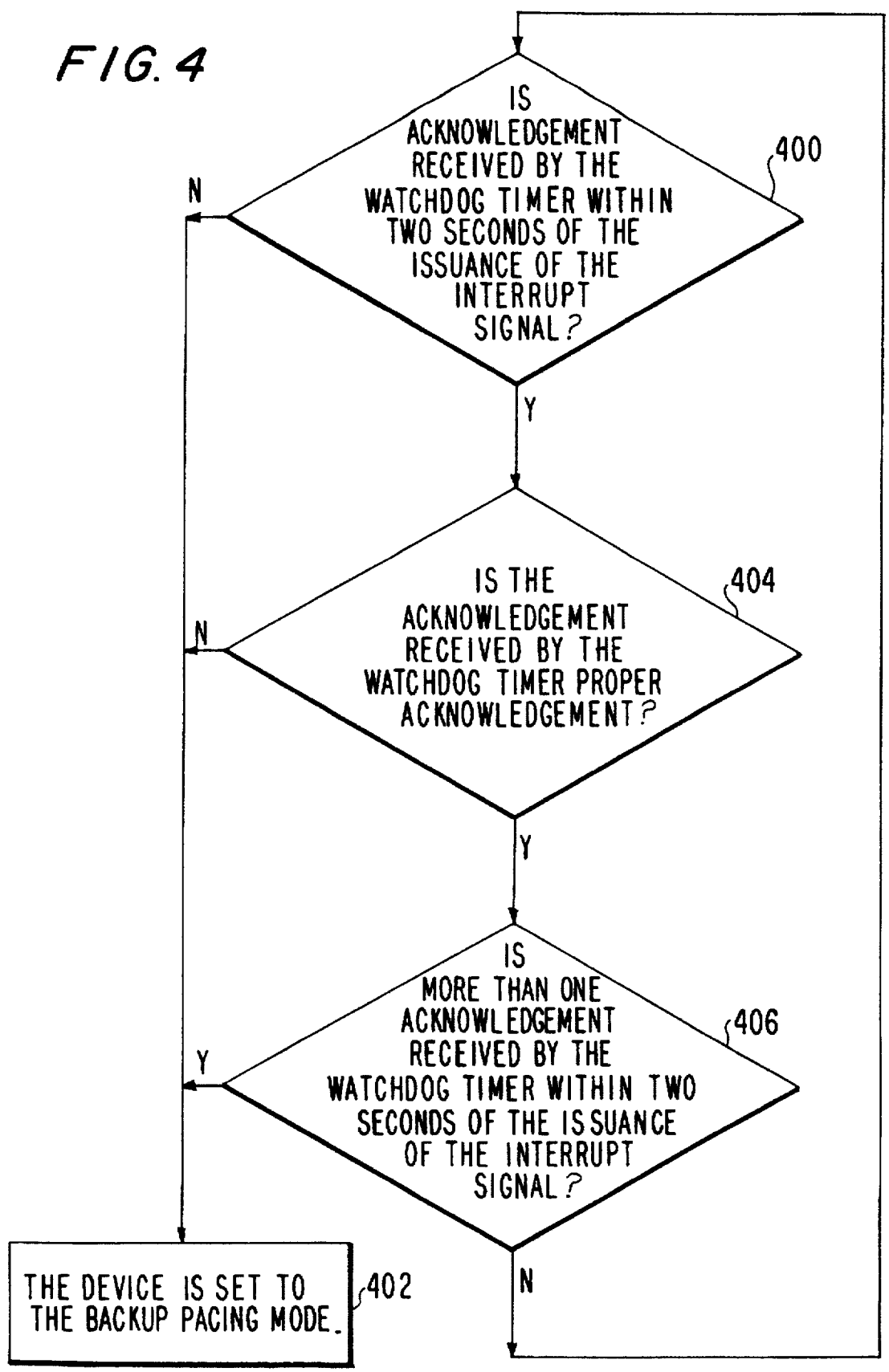
FIG. 4 is a flow diagram of an error detection sequence carried out by the watchdog timer circuit shown in FIG. 2.

As shown in FIG. 4, the watchdog timer circuit 218 (FIG. 2) first determines if acknowledgment is received within two seconds of the issuance of the interrupt signal at test 400. If acknowledgment has not been received within two seconds, the watchdog timer circuit 218 (FIG. 2) sets the device 100 to the backup pacing mode at step 402. If acknowledgment has been received within two seconds, the watchdog timer circuit 218 (FIG. 2) then checks if the acknowledgment is proper at test 404. If the acknowledgment is not proper, the watchdog timer circuit 218 (FIG. 2) switches the device 100 to the backup pacing mode at step 402. An acknowledgment is not proper if the microprocessor 202 (FIG. 2) does not provide the 6-bit key to the address specified by the 2-bit address code, both of which were retrieved during the previous acknowledgment. If the acknowledgment is proper, the watchdog timer circuit 218 (FIG. 2) then determines if more than one acknowledgment has been received at test step 406. If more than one acknowledgment has been received, the watchdog timer circuit 218 (FIG. 2) switches the device 100 to the backup pacing mode at step 402. More than one acknowledgment may be received if the microprocessor 202 (FIG. 2) is not functioning correctly. If the acknowledgment is proper, the process begins again with the issuance of a new interrupt signal.

If the microprocessor 202 (FIG. 2) is functioning correctly, it will properly acknowledge the interrupt signal to the watchdog timer circuit 218 (FIG. 2) within two seconds. However, if the microprocessor 202 (FIG. 2) has failed or is functioning incorrectly (which may, for example, be caused by a weakened battery), it may not properly acknowledge the interrupt signal to the watchdog timer circuit 218 (FIG. 2). When this occurs, the watchdog timer circuit 218 (FIG. 2) detects the error and implements backup pacing. The watchdog timer circuit 218 (FIG. 2) thus may prevent the device 100 from delivering inappropriate pacing or cardioversion/defibrillation therapy to the patient's heart 106, thereby increasing the safety of the device 100.

It will be clear to those skilled in the art that passwords other than the 8-bit password described above may be used in accordance with the present invention. For example, the password could comprise a key having 8 bits which are randomly generated with no address code. In this case, there would be only one address in the watchdog timer circuit 218 (FIG. 2) to which the key would be written, and a proper acknowledgment would require writing the 8-bit key to this address.

It will also be clear to those skilled in the art that the interval between interrupt signals issued by the real time clock logic 222 (FIG. 2) can be a value other than two seconds. For example, the interrupt signal could be sent every one second. It is, however, important that the signal be frequent enough to allow the backup pacing circuitry to be activated without an undue delay between pacing pulses.

Referring again to FIG. 2, further error checking is provided by the parity generator 214 and the parity checker 216. The parity generator 214 preferably is a conventional hardwired circuit which generates a parity bit for data which are stored in the internal RAM 210 or the external RAM 144 (FIG. 1). The parity checker 216 preferably is a conventional hardwired circuit which checks the parity bit of data which are read from the internal RAM 210 or the external RAM 144 (FIG. 1).

The microprocessor 202 preferably manipulates data in 8-bit bytes. When data are stored in the external RAM 144 (FIG. 1) or the internal RAM 210 the parity generator 214 generates a ninth bit which indicates the parity of the 8 data bits. The 8 data bits and the parity bit are then stored in the external RAM 144 (FIG. 1) or the internal RAM 210. Information is thus stored in 9-bit units—8 data bits and the corresponding parity bit. The parity bit preferably can be generated in a conventional manner, such as by determining the number of "ones" in the 8 data bits. If there are an even number of "ones," the parity bit is set to "one," while an odd number of "ones" causes the parity bit to be set to "zero." Alternatively, the parity bit could be chosen so as to produce an even number of "ones" in the combined data and parity bits.

When data are retrieved from the internal RAM 210 or the external RAM 144 (FIG. 1) the parity checker 216 checks the parity bit. If the parity bit is not correct, the parity checker 216 generates an error signal indicating that a parity error has been detected. The error signal is received by the watchdog timer circuit 218, which then switches the device 100 to the appropriate mode. The detection of a parity error may indicate that the data stored in the memory devices are corrupt and should not be used. If a parity error is detected while the device is in the normal mode, the device 100 is set to the intermediate mode either by the watchdog timer circuit 218 or other switching circuitry (not shown). If a parity error is detected while the device is in the intermediate mode, the device 100 is set to the backup mode either by the watchdog timer circuit 218 or other switching circuitry (not shown). If the parity bit is correct, the microprocessor 202 is allowed to proceed with retrieving the data.

Parity error checking in accordance with the present invention thus overcomes the deficiencies of previous devices. In particular, parity error checking is preferably performed on all data stored in the internal RAM 210 and the external RAM 144 (FIG. 1), rather than just on program instructions stored in RAM. The device 100 thus increases the safety of the patient by providing increased error detection.

Still further error checking is done by the address decoder 220. The address decoder 220 is preferably a conventional hardwired circuit. Before the microprocessor 202 accesses an address location of the internal RAM 210, the ROM 212, or the external RAM 144, the address decoder 220 decodes the address and determines if the address is a proper address. An example of an improper address is an address which is higher than the highest valid address location. If the address decoder 220 detects the microprocessor 202 attempting to access an improper address, the address decoder 220 sends an error signal to the watchdog timer circuit 218. If the address location is determined to be invalid and the device 100 is in the normal mode, the device 100 is set to the intermediate mode either by the watchdog timer circuit 218 or other switching circuitry (not shown). If the device 100 is in the intermediate mode and an address error is detected, the device 100 is set to the backup mode either by the watchdog timer circuit 218 or other switching circuitry (not shown).

Yet another type of error detection is provided by the opcode checker 226. The opcode checker 226 preferably is a conventional hardwired circuit. The opcode checker checks each opcode (which the microprocessor 202 attempts to fetch) in order to determine if the opcode is valid. When the microprocessor 202 is about to fetch an opcode from the ROM 212, the internal RAM 210, or the external RAM 144 (FIG. 1), the opcode checker 226 is notified via the data bus 204. The opcode checker then determines if the opcode is valid. If the opcode is not valid an error signal is generated and sent to the watchdog timer circuit 218. If the opcode is not valid and the device 100 is in the normal mode, the device 100 is set to the intermediate mode either by the watchdog timer circuit 218 or other switching circuitry (not shown). If an opcode error is detected while the device 100 is in the intermediate mode, the device 100 is set to the backup mode either by the watchdog timer circuit 218 or other switching circuitry (not shown). If, however, the opcode is determined to be valid, the microprocessor 202 is allowed to complete the fetch of the opcode.

In a preferred embodiment of the present invention, each opcode comprises 8 bits. This gives a total of 256 different 8-bit opcodes which can be used by the microprocessor 202. In a preferred embodiment, a relatively small number of the 256 opcodes available are unused and therefore invalid. Use of such an invalid opcode may cause the microprocessor 202 to function improperly, possibly causing the device to deliver inappropriate pacing therapy to the patient's heart. In a preferred embodiment, the opcode checker 226 determines if the opcode which the microprocessor 202 is about to fetch is one of the unused opcodes by comparing the opcode to each of the unused opcodes and determining if there is a match. If the fetched opcode matches one of the unused opcodes, then the fetched opcode is invalid. If there is not a match, the opcode is a valid opcode.

Figure 5:
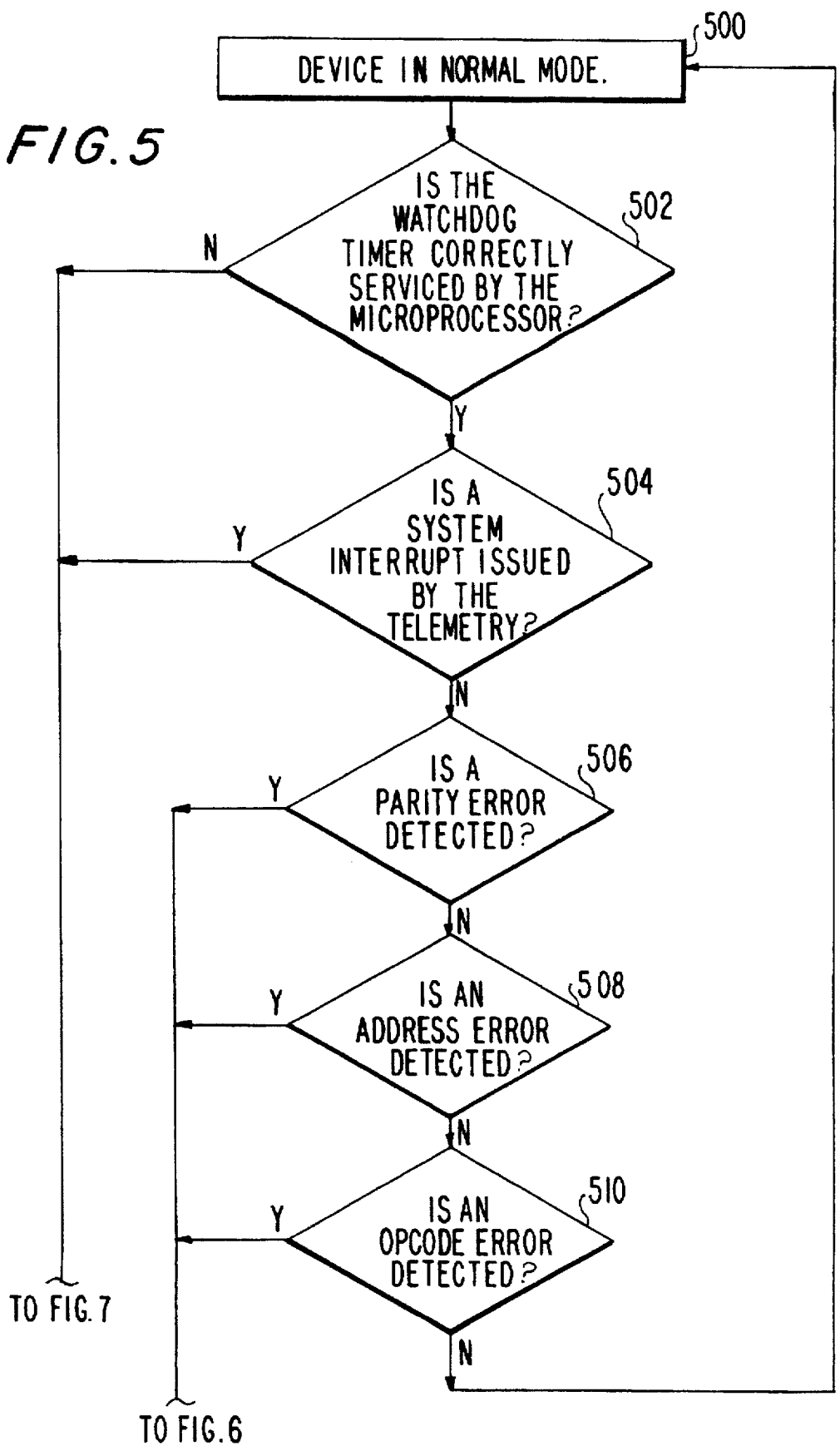
FIGS. 5–7 are flow diagrams of a fault detection sequence carried out by the watchdog timer circuit shown in FIG. 2 in order to provide switching between modes in accordance with the present invention.

FIG. 5 shows the error checking routine which is carried out by the watchdog timer circuit 218 (FIG. 2) while the device 100 is in the normal mode. There are two errors which, if detected while the device 100 is in the normal mode at step 500, cause the device to enter the backup pacing mode. First, if the watchdog timer circuit 218 (FIG. 2) is not correctly serviced by the microprocessor 202 (FIG. 2) at test 502, the watchdog timer circuit 218 (FIG. 2) sets the device 100 to the backup pacing mode. The tests carried out by the watchdog timer circuit 218 (FIG. 2) in order to determine if it is correctly serviced by the microprocessor 202 (FIG. 2) are described above in reference to FIG. 4. Second, if a system interrupt is received from the telemetry circuit 112 (FIG. 1) at test 504, the watchdog timer circuit 218 (FIG. 2) sets the device 100 to the backup pacing mode.

If a parity error, address error, or opcode error are detected while the device 100 is in the normal mode, the watchdog timer circuit 218 (FIG. 2) sets the device 100 to the intermediate mode. At test 506 the watchdog timer circuit 218 (FIG. 2) determines if an error signal has been received from the parity checker 216 (FIG. 2). If an error signal has been received by the watchdog timer circuit 218 (FIG. 2) from the parity checker 216 (FIG. 2), the watchdog timer circuit 218 (FIG. 2) sets the device 100 to the intermediate mode. At test 508 the watchdog timer circuit 218 (FIG. 2) determines if an error signal has been received from the address decoder 220 (FIG. 2). If an error signal has been received by the watchdog timer circuit 218 (FIG. 2) from the address decoder 220 (FIG. 2), the watchdog timer circuit 218 (FIG. 2) sets the device 100 to the intermediate mode. At test 510 the watchdog timer circuit 218 (FIG. 2) determines if an error signal has been received from the opcode checker 226 (FIG. 2). If an error signal has been received by the watchdog timer circuit 218 (FIG. 2) from the opcode checker 226 (FIG. 2), the watchdog timer circuit 218 (FIG. 2) sets the device 100 to the intermediate mode. If no errors are detected, the device 100 remains in the normal mode and the error checking routine of FIG. 5 is repeated by the watchdog timer circuit 218 (FIG. 2).

Figure 6:
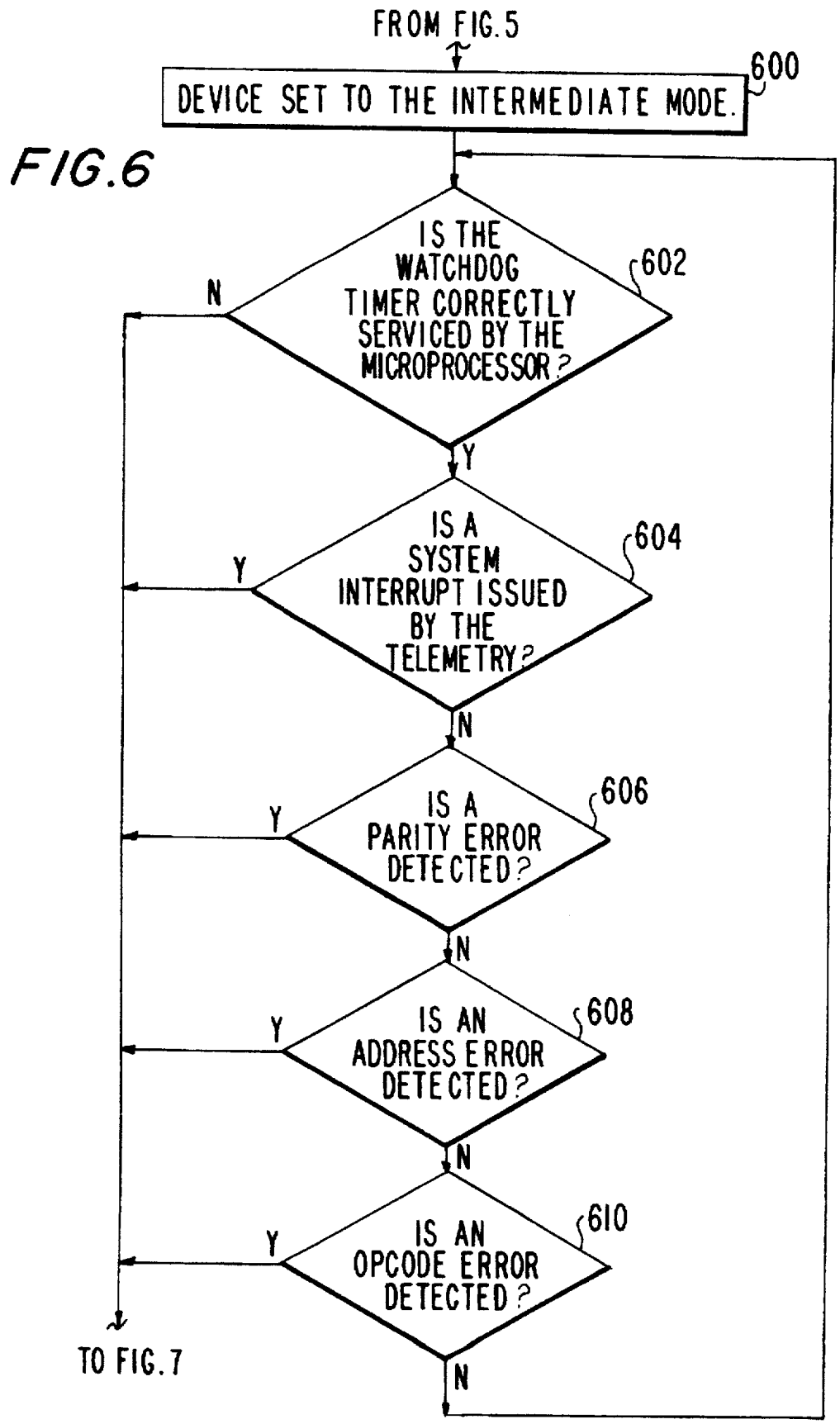

As shown in FIG. 6, while the device 100 is in the intermediate mode at step 600, if the watchdog timer circuit 218 (FIG. 2) is not correctly serviced by the microprocessor 202 (FIG. 2) at test 602, the watchdog timer circuit 218 (FIG. 2) sets the device 100 to the backup pacing mode. Again, the tests carried out by the watchdog timer circuit 218 (FIG. 2) in order to determine if it is correctly serviced by the microprocessor 202 (FIG. 2) are described above with reference to FIG. 4. If a system interrupt is received from the telemetry circuit 112 (FIG. 1) at test 604, the watchdog timer circuit 218 (FIG. 2) sets the device 100 to the backup pacing mode.

If a parity error, address error, or opcode error is detected while the device 100 is in the intermediate mode, the watchdog timer circuit 218 (FIG. 2) sets the device 100 to the backup pacing mode. At test 606 the watchdog timer circuit 218 (FIG. 2) determines if an error signal has been received from the parity checker 216 (FIG. 2). If an error signal has been received by the watchdog timer circuit 218 (FIG. 2) from the parity checker 216 (FIG. 2), the watchdog timer circuit 218 (FIG. 2) sets the device 100 to the backup pacing mode. At test 608 the watchdog timer circuit 218 (FIG. 2) determines if an error signal has been received from the address decoder 220 (FIG. 2). If an error signal has been received by the watchdog timer circuit 218 (FIG. 2) from the address decoder 220 (FIG. 2), the watchdog timer circuit 218 (FIG. 2) sets the device 100 to the backup pacing mode. At test 610 the watchdog timer circuit 218 (FIG. 2) determines if an error signal has been received from the opcode checker 226 (FIG. 2). If an error signal has been received by the watchdog timer circuit 218 (FIG. 2) from the opcode checker 226 (FIG. 2), the watchdog timer circuit 218 (FIG. 2) sets the device 100 to the backup pacing mode. If no errors are detected, the device 100 remains in the intermediate mode and the error checking routine of FIG. 6 is repeated by the watchdog timer circuit 218 (FIG. 2).

Figure 7:
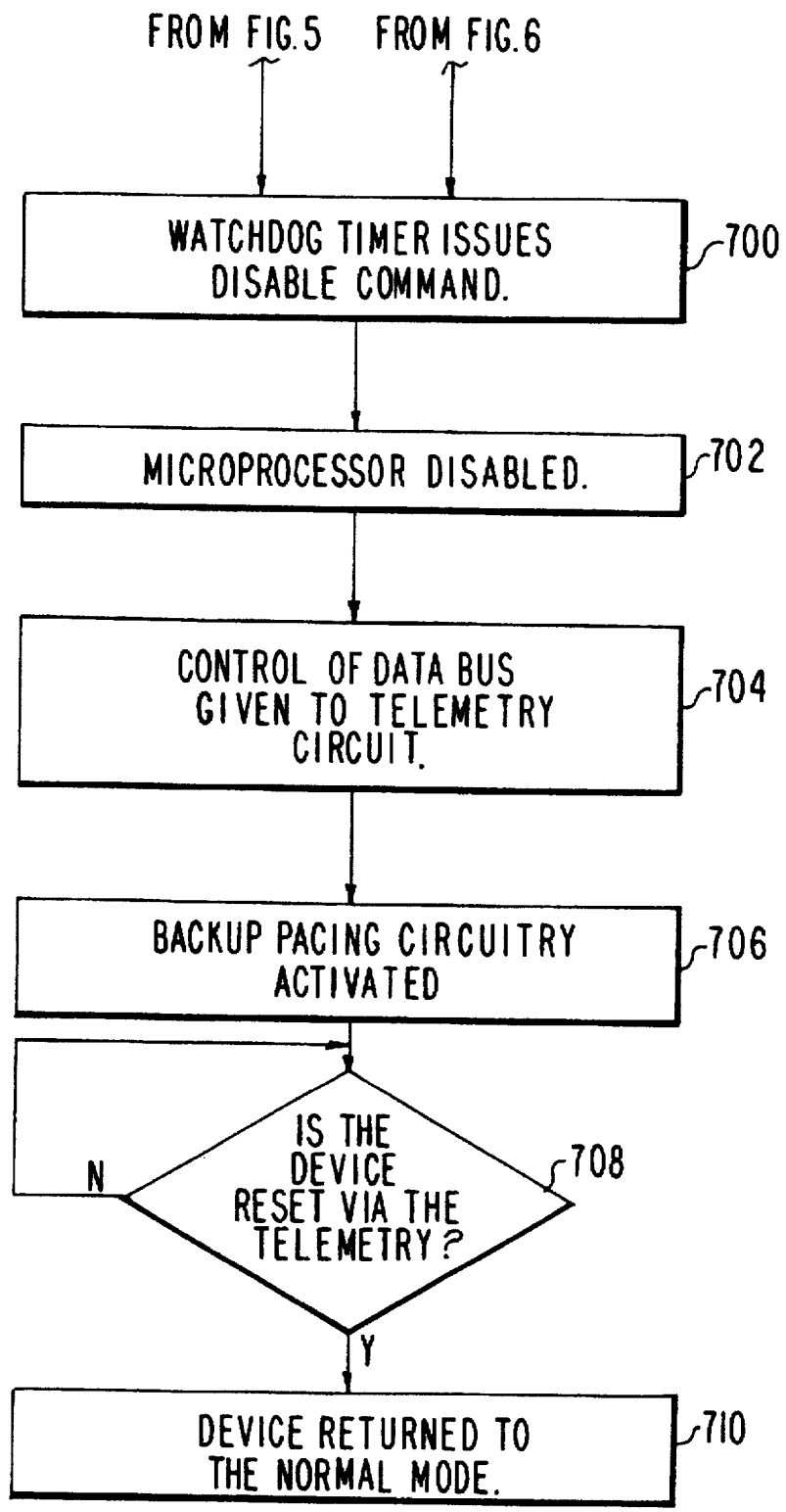

The sequence of steps of FIG. 7 is preferably carried out by the watchdog timer circuit 218 (FIG. 2) in order to set the implantable cardiac stimulating device 100 to the backup pacing mode. First, the watchdog timer circuit 218 (FIG. 2) issues a disable command at step 700. This command disables the microprocessor 202 (FIG. 2) at step 702 and gives control of the data bus 204 (FIG. 2) to the telemetry circuit 140 (FIG. 1) at step 704. The watchdog timer circuit 218 (FIG. 2) then activates the backup pacing circuit 118 (FIG. 1) at step 706 which preferably administers VVI pacing to the patient's heart 106. The implantable cardiac stimulating device 100 preferably cannot exit the backup pacing mode until the device 100 is reset via the telemetry circuit 140 (FIG. 1) at test 708. Once a reset is issued, the device 100 preferably is returned to the normal mode at step 710.

In addition to the error detection methods and circuitry described above, implantable cardiac stimulating device 100 also prevents errors which may be caused by transient electrical signals generated during the delivery of a cardioversion or defibrillation shock. Referring again to FIG. 2, during the delivery of a cardioversion or defibrillation shock, signals generated by the microprocessor 202 may be subjected to transient electrical signals. These transient electrical signals may cause the signals produced by the microprocessor 202 to be altered. In order to prevent errors from occurring due to these transient electrical signals, the microprocessor 202 is shut down during the delivery of a cardioversion or defibrillation shock as described in detail below.

Additional error protection during the delivery of a cardioversion or defibrillation shock is provided by the gating circuit 206. The gating circuit 206 controls access to the interrupt registers 208 of the microprocessor 202. The interrupt registers 208 are used to alert the microprocessor 202 that an event has occurred that may require the immediate attention of the microprocessor 202. For example, sensing circuit 112 (FIG. 1) may send an interrupt signal to the microprocessor 202 if an electrical signal from the patient's heart 106 is detected. As another example, interrupt signals may also be issued by the telemetry circuit 140 (FIG. 1).

During the delivery of a cardioversion or defibrillation shock, transient electrical signals may cause any one of the interrupt registers 208 inadvertently to be set. This in turn will cause the microprocessor 202 to respond to the interrupt after the delivery of the cardioversion or defibrillation shock. In responding to such a false interrupt the microprocessor 202 may cause the device 100 to apply inappropriate pacing therapy or cardioversion/defribillation shocks to the patient's heart 106. In accordance with the present invention, the gating circuit 206 is provided to prevent transient electrical signals from setting the interrupt registers, thereby increasing the safety of the patient.

The gating circuit 206 preferably is a conventional hard-wired circuit which can switch between two positions. The first position of gating circuit 206 allows interrupt signals on the data bus 204 intended for the interrupt registers 208 to reach the interrupt registers 208. The second position of the gating circuit 206 does not permit interrupt signals on the data bus 204 to reach the interrupt registers 208. The gating circuit 206 is controlled by the microprocessor 202, whereby the microprocessor 202 is able to select whether the gating circuit 206 is in the first or second position.

Figure 8:
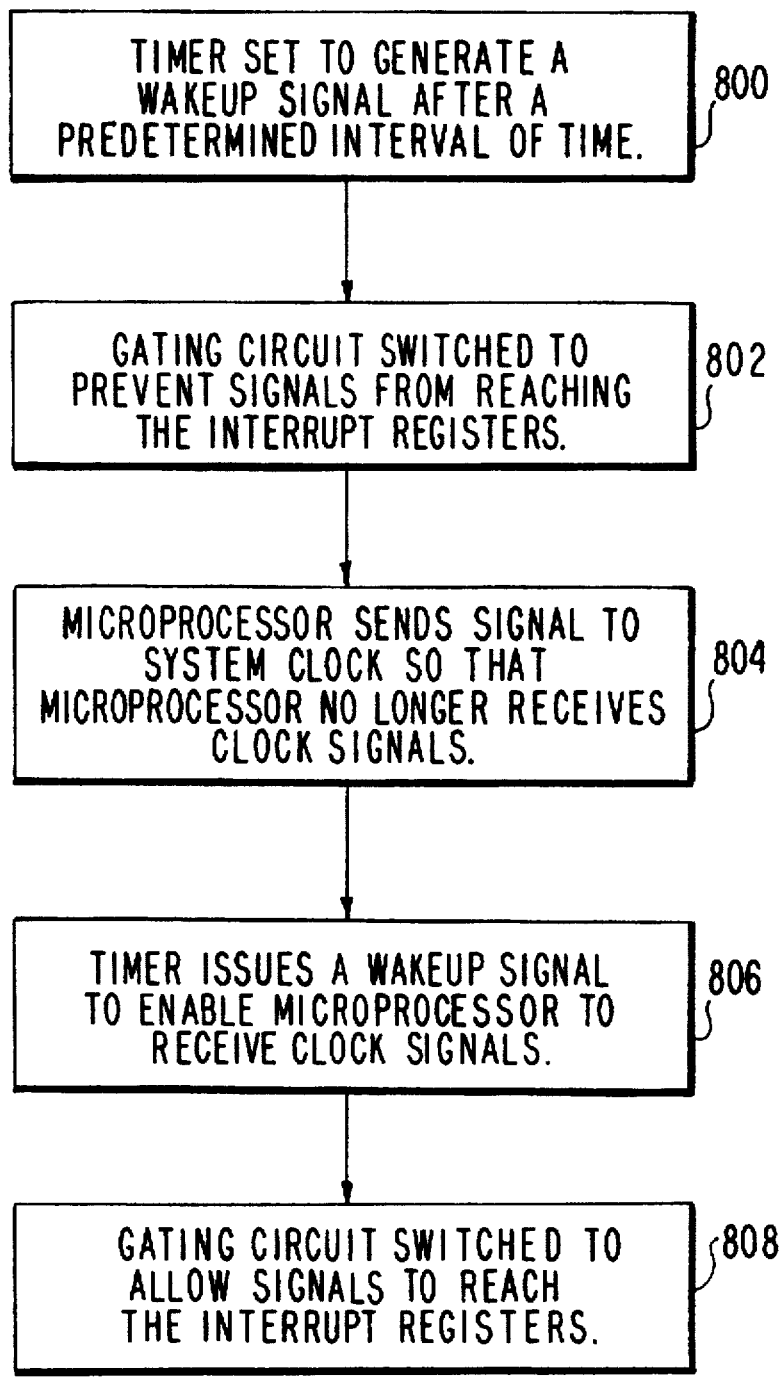
FIG. 8 is a flow diagram for the shutdown of the microprocessor shown in FIG. 2 during delivery of a cardioversion or defibrillation shock.

As shown in FIG. 8, in accordance with the present invention, just prior to the delivery of a cardioversion or defibrillation shock to the patient's heart 106, the microprocessor 202 (FIG. 2) programs the timer 224 (FIG. 2) at step 800 to send a wakeup signal to the system clock generator 228 (FIG. 2). The timer 224 (FIG. 2) is programmed so that the wakeup signal is sent to the system clock generator 228 (FIG. 2) after a predetermined amount of time has passed, which predetermined amount of time is measured from the time at which the timer 224 (FIG. 2) is programmed. The microprocessor 202 (FIG. 2) then sends a signal to the gating circuit 206 (FIG. 2) at step 802 which causes the gating circuit 206 (FIG. 2) to switch to the second position in which signals are prevented from reaching the interrupt registers 208 (FIG. 2). After switching the gating circuit 206 (FIG. 2), the microprocessor 202 (FIG. 2) generates a signal at step 804 which prevents the microprocessor 202 (FIG. 2) from receiving clock signals from the system clock generator 228 (FIG. 2), thus halting the microprocessor 202 (FIG. 2). After a predetermined amount of time which is longer than the time required to deliver the cardioversion or defibrillation shock, the timer 224 (FIG. 2) issues the wake-up signal which causes clock signals from the system clock generator 228 (FIG. 2) to be received by the microprocessor 202 (FIG. 2) at step 806. The microprocessor 202 (FIG. 2) is then able to continue processing. The microprocessor 202 (FIG. 2) then sets the gating circuit 206 (FIG. 2) back to the first position in which signals are allowed to reach the interrupt registers 208 (FIG. 2) at step 808. In this manner, neither the interrupt registers 208 (FIG. 2) nor the signals produced by the microprocessor 202 (FIG. 2) are subjected to the transient electrical signals generated during the delivery of a cardioversion or defibrillation shock.

Referring again to FIG. 2, it is preferable to provide at least one interrupt register which preferably cannot be switched by the gating circuit 206. Preferably, a reset register (not shown) which is able to reset the microprocessor 202 cannot be switched off by the gating circuit 206. It is therefore possible to reset the microprocessor 202 should the microprocessor 202 malfunction and leave the gating circuit 206 in the second position in which the interrupt registers 208 are not accessible.

It will be readily apparent to those skilled in the art that the microprocessor 202 can be shut down during the delivery of a cardioversion or defibrillation shock without isolating the interrupt registers 208. It will also be apparent that the interrupt registers 208 can be isolated during the delivery of a cardioversion or defibrillation shock even if the microprocessor 202 is not shut down.

Figure 9:
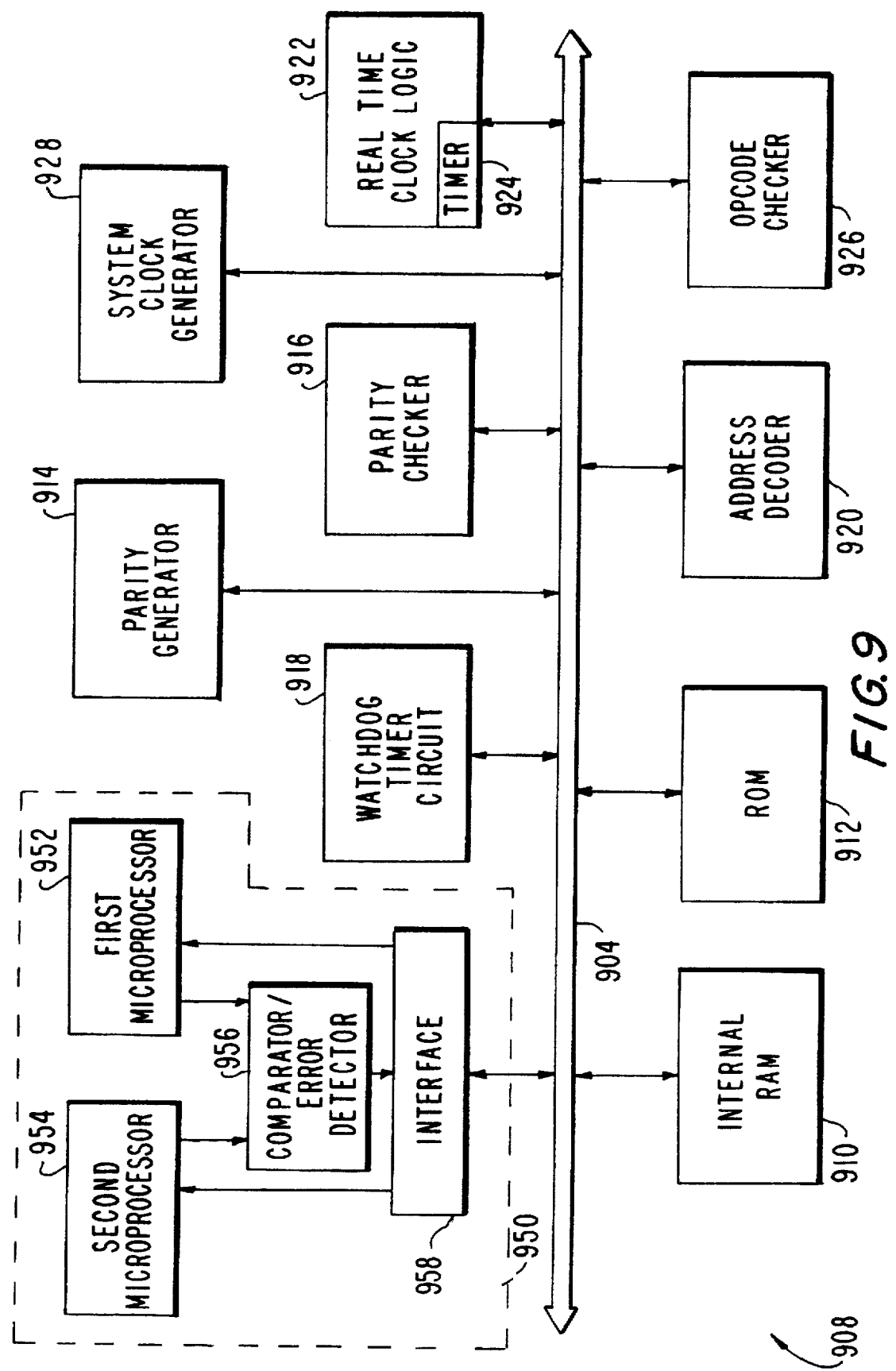
FIG. 9 is a schematic diagram of an alternative processing and control unit that includes redundant microprocessors in accordance with the present invention.

An alternative embodiment of a processing and control unit (suitable for use as the processing and control unit 114 of FIG. 1) is shown in FIG. 9. Processing and control unit 908 includes a data bus 904, an internal RAM 910, a ROM 912, a parity generator 914, a parity checker 916, a watchdog timer circuit 918, an address decoder 920, a real time clock logic 922, a timer 924, an opcode checker 926, and a system clock generator 928, which work in substantially the same manner as described above in connection with the processing and control unit 200 of FIG. 2 and therefore will not be described further.

In this embodiment, however, further error checking is provided by a microprocessor unit 950. The microprocessor unit 950 includes two microprocessors—a first microprocessor 952 and a second microprocessor 954, each of which is connected to a comparator/error detector 956 and an interface 958 which communicates with the data bus 904. Each of the first and second microprocessors 952, 954 also preferably has a gating circuit (not shown) which operates in substantially the same manner as the gating circuit 206 (FIG. 2) described above.

In the processing and control unit 200 of FIG. 2, all signals which are intended for the microprocessor 202 simply pass directly from the data bus 204 to the microprocessor. However, in the processing and control unit 908 of FIG. 9, all signals which are directed to the microprocessor unit 950 are first received by the interface 958.

Figure 10:
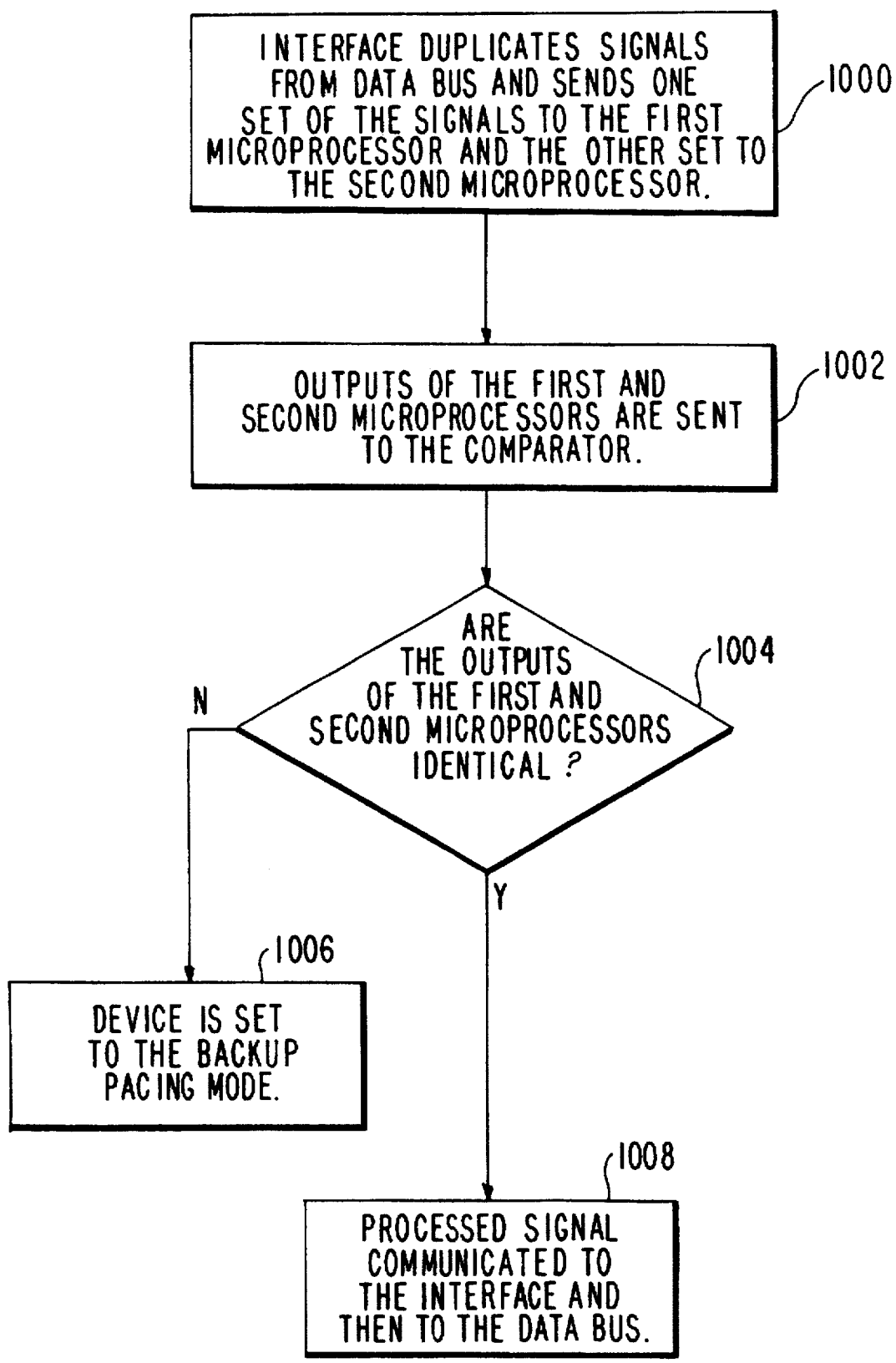
FIG. 10 is a flow diagram for the error checking performed in order to determine if the first and second microprocessors of FIG. 9 are functioning correctly.

As shown in FIG. 10, the interface 958 (FIG. 9) duplicates the signals received from the data bus 904 (FIG. 9) and sends one set of the signals to the first microprocessor 952 (FIG. 9) and another set of the signals to the second microprocessor 954 (FIG. 9) at step 1000. After the signals are processed by each of the first microprocessor 952 (FIG. 9) and the second microprocessor 954 (FIG. 9), the respective outputs are sent to the comparator/error detector 956 (FIG. 9) at step 1002. The comparator/error detector 956 (FIG. 9) compares the outputs of the first and second microprocessors 952, 954 (FIG. 9) in order to determine if outputs of the first and second microprocessors 952, 954 (FIG. 9) are substantially identical at step 1004. The comparator/error detector 956 (FIG. 9) determines that the microprocessors 952, 954 (FIG. 9) are not functioning correctly if the processed signals from the first and second microprocessors 952, 954 (FIG. 9) are not substantially identical. Accordingly, the comparator/error detector 956 (FIG. 9) determines that the microprocessors 952, 954 (FIG. 9) are functioning correctly if the processed signals from the first and second microprocessors 952, 954 (FIG. 9) are substantially identical.

If the comparator/error detector 956 (FIG. 9) determines that the outputs from the microprocessors 952, 954 (FIG. 9) are not substantially identical, the comparator/error detector 956 (FIG. 9) issues an error detection signal which is received by the watchdog timer circuit 918 (FIG. 9) and causes the device 100 to enter the backup pacing mode at step 1006 (i.e., steps 700 through 710 of FIG. 7 are carried out; however, in this embodiment both microprocessors are shut down). Therefore, a malfunction of either the first or second microprocessor 952, 954 (FIG. 9) causes both microprocessors 952, 954 (FIG. 9) to be disabled and the device 100 to enter the backup pacing mode. If the device 100 is in either the normal mode or the intermediate mode and the comparator/error detector 956 (FIG. 9) detects an error, the device 100 is put in the backup pacing mode.

If, however, the comparator/error detector 956 (FIG. 9) determines that the outputs of the first and second microprocessors 952, 954 (FIG. 9) are substantially identical, the processed signal is communicated to the interface 958 (FIG. 9) and then to the data bus 904 (FIG. 9) at step 1008.

Thus, an implantable cardiac stimulating device having safety optimization apparatus and methods in order to prevent inappropriate electrical stimulation from being delivered to a patient's heart has been described. Those skilled in the art will understand that the invention can be practiced in other than the described embodiments, which are presented for purposes of illustration and not of limitation, and the present invention is limited only by the claims which follow.

What is claimed is:

1. An implantable cardiac stimulating device comprising:

a first microprocessor;

a second microprocessor;

a primary pacing circuit;

a backup pacing circuit;

a comparator electrically coupled to each of the first and second microprocessors for receiving signals therefrom;

switching circuitry, coupled to each of the comparator, the primary pacing circuit, and the backup pacing circuit;

an interface coupled to each of the comparator and the first and second microprocessors; and a data bus coupled to the interface, the data bus receiving signals from at least one signal source, and the interface receiving the signals from the data bus and communicating the signals to each of the first and second microprocessors, the first microprocessor processing the signals to produce a first processed signal, the second microprocessor processing the signals to produce a second processed signal, each of the first and second processed signals being communicated to the comparator, the comparator comparing the first and second processed signals in order to determine if the first and second microprocessors are functioning correctly; wherein:

the switching circuitry activates the backup pacing circuit and deactivates the primary pacing circuit in response to a determination that the first and second microprocessors are not functioning correctly.

2. The device of claim 1, wherein the comparator determines that the first and second microprocessors are not functioning correctly if the first and second processed signals are not substantially identical.

3. The device of claim 1, wherein, if the first and second microprocessors are not functioning correctly, the comparator outputs an error signal, and wherein the first and second microprocessors are disabled in response to the error signal.

4. A method of operating an implantable cardiac stimulating device, the implantable stimulating device having a first microprocessor, a second microprocessor, a comparator electrically coupled to each of the first and second microprocessors for receiving signals therefrom, a data bus for transferring signals to and from at least one signal source and each of the first and second microprocessors, a primary pacing circuit, and a backup pacing circuit, the method comprising the steps of:

communicating a signal from the data bus to each of the first and second microprocessors, the first microprocessor processing the signal to produce a first processed signal, and the second microprocessor processing the signal to produce a second processed signal;

communicating each of the first and second processed signals to the comparator;

comparing the first and second processed signals using the comparator in order to determine if the first and second microprocessors are functioning correctly; and deactivating the primary pacing circuit and activating the backup pacing circuit in response to a determination that the first and second microprocessors are not functioning correctly.

5. The method of claim 4, wherein the comparing step comprises the step of:
determining that the microprocessors are not functioning correctly when the first and second processed signals are not substantially identical.

6. The method of claim 4, further comprising the step of:
using a timer circuit to disable each of the first and second microprocessors when the comparator determines that the first and second microprocessors are not functioning correctly.

* * * * *